United States Patent
Kaga et al.

(10) Patent No.: US 7,323,697 B2
(45) Date of Patent: Jan. 29, 2008

(54) WAFER ALIGNMENT METHOD FOR DUAL BEAM SYSTEM

(75) Inventors: Hiroyasu Kaga, Mito (JP); Hiroyuki Suzuki, Hitachinaka (JP); Yutaka Hojyo, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 267 days.

(21) Appl. No.: 11/258,939

(22) Filed: Oct. 27, 2005

(65) Prior Publication Data
US 2006/0091321 A1 May 4, 2006

(30) Foreign Application Priority Data
Oct. 28, 2004 (JP) ............................. 2004-314089

(51) Int. Cl.
*H01J 37/28* (2006.01)
(52) U.S. Cl. .................. 250/491.1; 250/306; 250/307; 250/309
(58) Field of Classification Search ............. 250/491.1, 250/306, 307, 309
See application file for complete search history.

(56) References Cited

U.S. PATENT DOCUMENTS

| 6,039,000 A | 3/2000 | Libby et al. |
| 7,009,192 B2 * | 3/2006 | Suzuki et al. ............. 250/491.1 |
| 2006/0219953 A1 * | 10/2006 | Carleson ................. 250/492.21 |

FOREIGN PATENT DOCUMENTS

| JP | 2002-503870 A | 2/2002 |
| WO | WO 99/41765 | 8/1999 |

* cited by examiner

*Primary Examiner*—Kiet T. Nguyen
(74) *Attorney, Agent, or Firm*—McDermott Will & Emery LLP

(57) ABSTRACT

A gradient charged particle beam apparatus capable of moving highly accurately to a specific position by eliminating influences of warp inside a wafer surface is provided. A portion 46 having a mark 47 for aligning visual field alignment positioned in advance to the same horizontal and the same height as a stage plane as a reference point is arranged on a wafer holder. A height of an observation point on a sample is adjusted to the height of the mark 47 and the visual field of a gradient column is brought into conformity with the visual field of a vertical column by use of a known offset between the gradient column and the vertical column at that time.

13 Claims, 7 Drawing Sheets

FIG. 6A
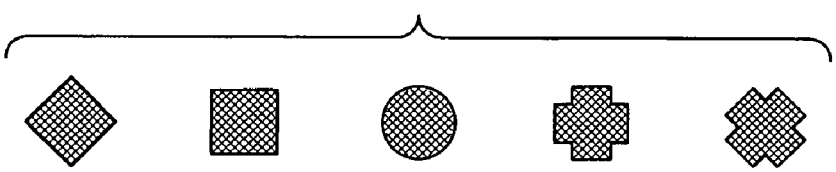
FIG. 6B  FIG. 6C  FIG. 6D
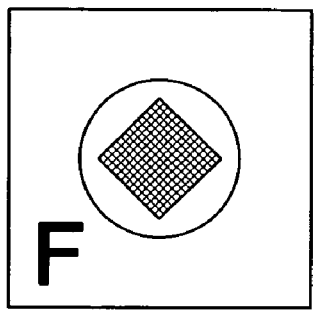 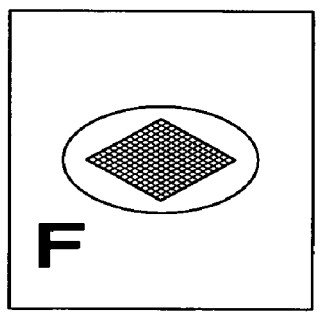 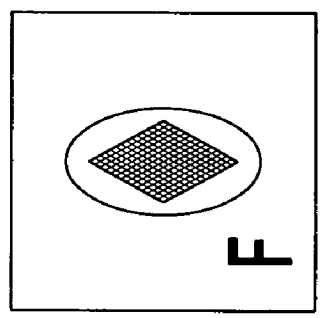
VERTICAL  OBLIQUE 45°  ROTATION OBLIQUE 45°

WAFER ALIGNMENT METHOD FOR DUAL BEAM SYSTEM

BACKGROUND OF THE INVENTION

1. Field of the Invention

This invention relates to a charged particle beam apparatus having a column inclined with respect to a sample surface.

2. Description of the Related Art

To observe or process a very fine pattern formed on a semiconductor wafer, charged particle beam apparatuses such as a scanning electron microscope (SEM) and a focused ion beam apparatus (FIB) have been used to this date.

JP-A-2002-503870 discloses an improved focused ion beam apparatus having a construction in which axes of two columns of FIB and SEM are inclined at 45° to a Z axis, their axes have a perpendicular relation and no offset exists between the axes.

JP-A-2002-503870 does not mention the case where offset exists between the axes of FIB and SEM. This reference does not mention the problem of deviation of visual fields of SEM and FIB resulting from the difference of a sample height and the problem of deviation of the visual fields after focus adjustment of a beam. Furthermore, the reference does not at all mention the problem of a read error of a position resulting from the difference of the height of an alignment point that is unavoidable in gradient columns.

In defect inspection of semiconductor wafers, it is necessary to analyze a defect position detected by an inspection apparatus by another apparatus. Because coordinates systems are different between these apparatuses (center of wafer coordinates system, rotation, distortion of X and Y, etc resulting from the difference of measurement system of stage), correction must be made by conducting wafer alignment between the apparatuses and then positioning. To move the stage to the defect position detected by the wafer inspection apparatus and to find out the defect from the screen, the defect must fall within at least the visual field of the image at the movement destination. To identify the defect, magnification capable of recognizing at least the defect is necessary. Therefore, the magnification necessary for identifying the defect is estimated. When the size of the defect becomes 0.1 µm, the size of the defect is 1 mm at magnification×10k and is displayed at 14 µm at an angle of view of 140 mm. The defect can be specified relatively easily when the defect can be enlarged up to 2 mm. This magnification is ×20 k and is display of 7 µm. Assuming that integration of devices further proceeds and the existing 90 nm node becomes 65 nm node in 2005 or 2006, the defect of the devices becomes smaller with the node. Therefore, to enlarge the defect of 65 nm to 2 mm and to search the defect, magnification ×30 k is approximately necessary and display of less than 5 µm is necessary. In other words, positioning accuracy of ±3 µm or below is necessary.

In ordinary wafer alignment executed by a column vertical to the wafer, the focus changes with the change of the wafer height but the position does not change. Therefore, positioning can be made with high accuracy by wafer alignment without taking the wafer height into consideration. In the case of the column apparatus inclined with respect to the wafer, however, the position changes depending on the height of the point at which wafer alignment is made. It is therefore necessary to always keep the wafer alignment point at a predetermined reference height. Nonetheless, the difference of the height exists inside the wafer surface because the wafer generally has warp.

When the beam of each of FIB and SEM is inclined to the axis Z perpendicular to the X, Y plane of the stage on which the wafer is put and when a point P1 at the height at which the point of intersection of the two beams exists as shown in FIG. 1, the point P1 can be observed without moving the stage. When the height of the observation point is not Z0, the observation visual fields of these two beams are different and the stage movement L is necessary for establishing focus of FIB on the same observation point when a point P2 at a certain height h is observed through SEM.

When SEM and FIB are used for wafer inspection as described above, the inspection apparatus must be move with accuracy of about 3 µm to a position designated by the defect inspection apparatus. In the case of the column apparatus perpendicular to the stage, the observation position (X, Y) doe not change even when the height of the observation point changes. Therefore, positioning can be made with accuracy of about 3 µm by executing wafer alignment. In the gradient column, however, the observation position (X, Y) changes when the height of the observation point changes because observation is oblique observation. When the processing object is the wafer, the wafer undergoes warp and distortion with the progress of the semiconductor process such as washing, exposure, development, vacuum deposition, etching, heat treatment and so forth. In consequence, warp of a ɸ300 mm wafer is as great as 200 µm. This warp results as such in the deviation of the visual field of the image in the case of the 45° gradient column. Consequently, alignment accuracy drops and eventually, positioning accuracy gets deteriorated. In this case, positioning accuracy drops unless the offset amount is correctly grasped.

SUMMARY OF THE INVENTION

It is an object of the invention to improve positioning accuracy in a charged particle beam apparatus having a gradient column.

To accomplish this object, a height of an adjustment point as a reference and its position are decided. A portion having a mark for aligning the visual fields is provided onto a stage and an offset between a column having an optical axis parallel to a Z axis and a column having an optical axis inclined to the Z axis is measured by using this mark.

An alignment method according to the invention is an alignment method in a charged particle beam apparatus including a stage capable of moving inside an XY plane and in a Z axis direction perpendicular to the XY plane while holding a sample, a first column having an optical axis parallel to the Z axis and a second column having an optical axis inclined to the Z axis, the method comprising the steps of positioning a mark at a reference height to a visual field center of the first column and calculating stage coordinates of the mark; positioning the mark to a visual field center of the second column and calculating the stage coordinates of the mark; and determining a difference between the stage coordinates of the mark by the first column and the stage coordinates of the mark by the second column as an offset between the visual field of the first column and the visual field of the second column.

To conduct alignment to a specific position on a sample, the alignment method includes the steps of moving the stage inside the XY plane and positioning a known mark on a sample to the visual field center of the first column; moving the stage by the offset; observing the known mark by the second column and determining a deviation amount from the visual field center; determining a height deviation of the sample from the reference height on the basis of the deviation amount; and moving the stage by the height deviation in the Z axis direction and adjusting a sample surface provided with the known mark to the reference height.

According to the invention, it is possible to eliminate influences of warp inside a wafer surface in a charged particle beam apparatus having a gradient column, to move with high accuracy the visual field to a specific position, to easily move the apparatus to the defect position obtained from a wafer inspection apparatus and to conduct defect analysis. When the beam apparatus has a gradient SEM column and a gradient FIB column, too, observation by SEM can be quickly switched to observation and processing by FIB.

The sample height can be automatically self-recovered to the height of the reference surface by conducting pre-adjustment by using the beam adjustment mark on the wafer holder before wafer alignment, and the problem of the change of the axes before and after the beam adjustment between FIB and SEM and the problem of deviation of the visual fields owing to the difference of the height of the observation point inside the wafer surface can be eliminated. Accuracy of wafer alignment in the gradient column can thus be improved.

Other objects, features and advantages of the invention will become apparent from the following description of the embodiments of the invention taken in conjunction with the accompanying drawings.

BRIEF DESCRIPTION OF THE DRAWINGS

FIGS. 6A, 6B, 6C and 6D show examples of 90° rotation object figures;

DESCRIPTION OF THE EMBODIMENT

An embodiment of the invention will be hereinafter explained with reference to the accompanying drawings.

Figure 1:
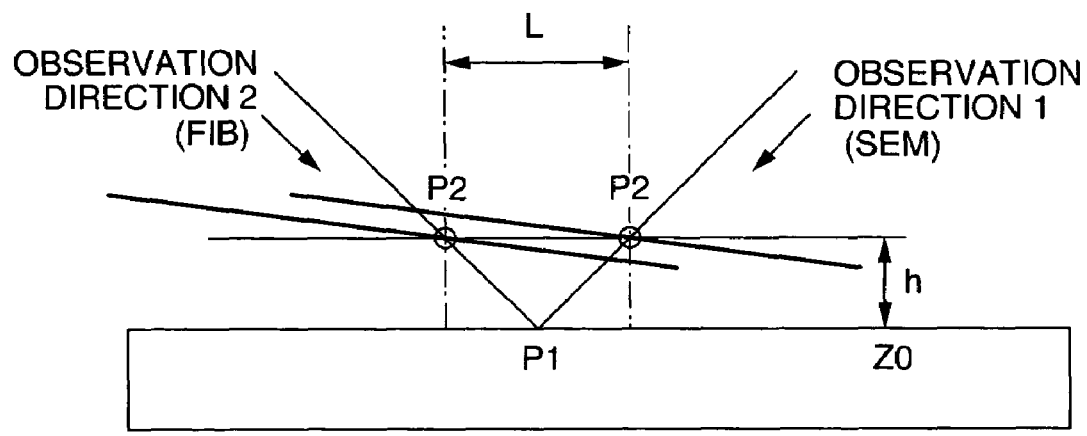
FIG. 1 is an explanatory view of an observation point of a gradient column.
Figure 2:
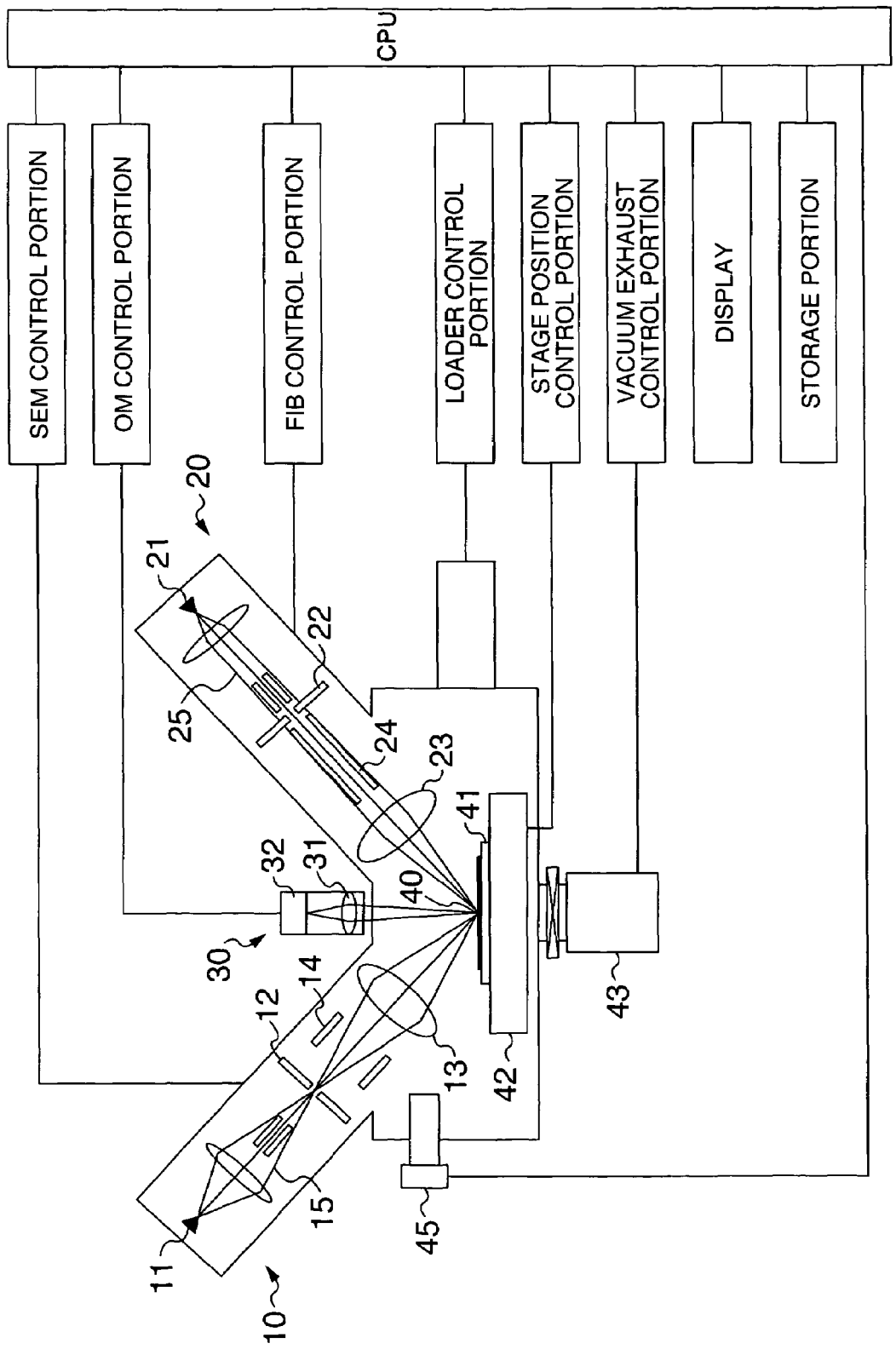
FIG. 2 is a schematic view showing a structural example of a gradient column charged particle beam apparatus according to the invention.

FIG. 2 shows a structural example of a gradient column charged particle beam apparatus according to the invention. This gradient column charged particle beam apparatus is a dual beam apparatus including an optical microscope (OM) and a column 30 that are perpendicular to a stage plane, and a scanning electron microscope (SEM) column 10 and a focusing ion beam (FIB) column 20 that are inclined with respect to the stage plane. A wafer 40 is held by a wafer holder 41 and is moved by a stage 42 having four axes of X, Y, Z and R. The position of the stage 42 is measured by a laser measuring system.

The SEM column 10 includes an electron gun 11 constituted by a Schottky emission electron source such as Zr/W, a beam control aperture 12 for controlling a beam current, a lens system 13 for contracting an electron beam 15 to the wafer 40 and a deflector 14 for scanning a beam on the wafer surface. The FIB column 20 includes an ion gun 21 constituted by a Ga liquid metal ion source, a beam control aperture 22 for controlling the ion beam 25, a lens system 23 for contracting the ion beam to the wafer and a deflector 24 for scanning a beam onto the wafer surface. The OM column 30 includes a light source, an objective lens 31 and a CCD camera 32.

The beams of FIB and SEM orthogonally cross each other and are inclined with respect to the Z axis perpendicular to the X-Y plane of the stage 42 on which the wafer is put. The explanation will be given hereby on the assumption that the optical axis of the SEM column exists inside the Z-Y plane passing through the origin and that the optical axis of the FIB column exists inside the Z-X plane passing through the origin. The incident direction of the electron beam of SEM describes an angle of 45° to the Z axis and the ion beam of FIB describes an angle of 45° to the Z axis. The optical axis of the OM column is parallel to the Z axis. Each beam need not always cross mutually at one point.

The signal acquired from a charged particle detector 45 is amplified and is then inputted in synchronism with a scan signal and its image is displayed on a display. The apparatus is subjected to centralized control by CPU and an OM control portion controls brightness and focus of OM. An SEM control portion controls acceleration of the electron beam, the beam current, focus and deflection. An FIB control portion controls acceleration of the ion beam, the beam current, focus and deflection. A loader control portion controls insertion/removal of the wafer holder and the stage control portion executes driving/positioning control of the stage 42 measured by laser measurement. A vacuum exhaust control portion controls a vacuum exhaust device 43.

Figure 3:
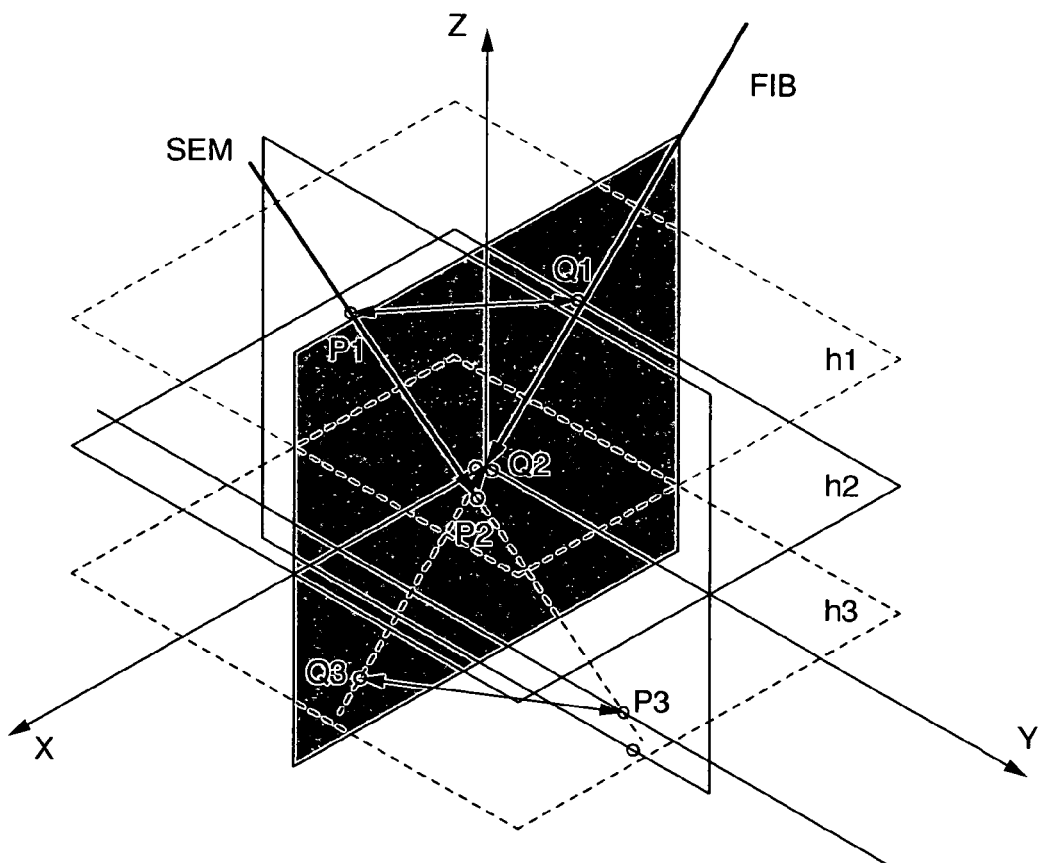
FIG. 3 is an explanatory view for explaining problems of the gradient column.

FIG. 3 illustrates the problems inherent to the gradient columns. This drawing shows the relation of observation points of SEM and FIB in the charged particle beam apparatus in which the beam axis of SEM exists on the X-Z plane and is inclined with respect to the Z axis and the beam axis of FIB exists on the X-Z plane and is inclined with respect to the Z axis. In the arrangement shown in the drawing, the observation point of SEM is P1 and that of FIB is Q1 when the height of the sample surface is h1 and their offset is P1Q1. When the height of SEM is h2, the observation point of SEM is P2, the observation point of FIB is Q2 and their offset is P2Q2. When the height of SEM is h3, the observation point of SEM is P3 and that of FIB is Q3 and their offset is P3Q3. In the case of the charged particle beam apparatus having a plurality of gradient columns, the offset (that can be expressed by vectors having different directions and different magnitudes) exists in accordance with the height of each observation point and the wafer must be moved by a distance corresponding to this offset.

When observation is made at the same observation point in the case of the gradient columns, the offset (that can be expressed by vectors having different directions and different magnitudes) exists in accordance with the height of the observation point as shown in FIG. 3 and the wafer must be moved by the distance corresponding to this offset. The wafer movement is troublesome and this problem can be solved by controlling the height in such a fashion that the height of the observation point inside the wafer does not change.

Generally, a wafer has warp and the warp of the wafer increases and an in-plane height difference is likely to increase as a fabrication process for fabricating a semiconductor device proceeds and as a wafer diameter becomes greater. A Z sensor using light (laser) is known as a method of measuring the wafer height. The object of the measurement of the wafer surface height is to control de-focusing but it not to improve alignment accuracy. Measurement accuracy of the Z sensor is not free from the problem of interference of the laser beam owing to a wiring pattern of the semiconductor device, etc and a measurement error of dozens of microns (μm) exists depending on wafers. Therefore, the problem of accuracy is not yet solved to correctly grasp the defect position. It might be possible to use an optical microscope for height alignment by utilizing shallowness of the depth of focus of the optical microscope. However, resolution and the depth of focus of the optical microscope are related with each other and to improve accuracy of height measurement, resolution must be increased and high magnification is necessary. Therefore, the distance (WD) between the wafer and the objective lens becomes small and interference with the objective lenses of FIB and SEM becomes space-wise unavoidable.

Because the X-Y coordinates of the stages of the wafer inspection apparatus and the inspection analysis apparatus are measured by a laser measuring system, they have extremely high positional accuracy of about 0.01 μm. To improve accuracy of wafer alignment in the gradient column apparatus having the laser measuring system, an accurate measurement method of the wafer surface height that replaces the Z sensor becomes necessary.

The difference of the moving distances on the coordinates system of the vertical column and on the coordinates system of the gradient column will be explained with reference to FIG. 4 when the stage is moved in the Z direction. In the coordinates systems shown in FIG. 4, the axis of the observation direction of SEM is inclined at 45° to the Z axis inside the Y-Z plane. Assuming that the coordinates system inherent to SEM is (Xs, Ys, Zs), the relational formula of rotation is expressed by the following formula. The Zs axis is an axis parallel to the observation direction of SEM, the Ys axis is an axis that is perpendicular to the Zs axis and exists inside the Y-Z plane and the Xs axis is an axis parallel to the X axis.

$$\begin{pmatrix} Xs \\ Ys \\ Zs \end{pmatrix} = \begin{pmatrix} 1 & 0 & 0 \\ 0 & \cos 45° & -\sin 45° \\ 0 & \sin 45° & \cos 45° \end{pmatrix} \begin{pmatrix} X \\ Y \\ Z + \Delta Z \end{pmatrix}$$ [Expression 1]

$$Xs = X$$

$$Ys = \frac{Y - Z}{\sqrt{2}} - \frac{\Delta Z}{\sqrt{2}}$$

$$Zs = \frac{Y + Z}{\sqrt{2}} + \frac{\Delta Z}{\sqrt{2}}$$

Therefore, when the stage is moved by ΔZ in the Z direction, the image does not move in the Xs direction in the SEM observation. However, the image moves by Ys=–ΔZ/√2 in the Ys direction and Zs=ΔZ/√2 in the Zs direction.

Assuming that the coordinates system inherent to OM is (Xom, Yom, Zom), on the other hand, Xom and Yom are in agreement with X and Y of the coordinates system of the stage and the Zom direction is in agreement with the Z axis of the stage. Therefore, the relational formula of the observation direction for OM can be expressed by the following formula.

$$\begin{pmatrix} Xom \\ Yom \\ Zom \end{pmatrix} = \begin{pmatrix} 1 & 0 & 0 \\ 0 & 1 & 0 \\ 0 & 0 & 1 \end{pmatrix} \begin{pmatrix} X \\ Y \\ Z + \Delta Z \end{pmatrix}$$ [Expression 2]

$$Xom = X$$

$$Yom = Y$$

$$Zom = Z + \Delta Z$$

In the case of OM, even when a change ΔZ occurs in the height direction, no influence occurs in the X and Y directions. In other words, to determine a specific position (X, Y) inside the wafer, X, Y information detected by OM is free from the influences of height and the (X, Y) position can be correctly determined even when any warp, hence, any change, exists in the height direction.

Generally, WD (distance between the objective lens and the sample) changes when the stage height Z is changed in an apparatus having a column for the charged particle beam that is perpendicular to the X, Y planes of the stage. Therefore, the focus condition changes but the observation position remains unaltered. In an apparatus having a column that is inclined to the wafer surface, however, the height is different at the observation point inside the wafer plane owing to the warp of the wafer and the stage position at the observation point observed in the vertical column and the stage position of the observation point observed in the same way in the gradient column are different. Because of this influence, accurate movement to the device defect position inside the wafer cannot be made. In the case of the oblique 45° gradient column described above, when the stage is moved by ΔZ in the Z direction, this movement results in Ys=–ΔZ/√2 in the Ys direction and Zs=ΔZ/√2 in the Zs direction in the SEM observation.

Because the axis changes in the beam adjustment (by causing the beam to pass through the center of the objective lens for focusing) in FIB and SEM, the visual field of the observation image changes before and after the beam adjustment. To solve this problem, the height of the adjustment point as the reference and its position are determined. Therefore, a portion having a mark for the visual field adjustment is provided onto the wafer holder.

Figure 5A:
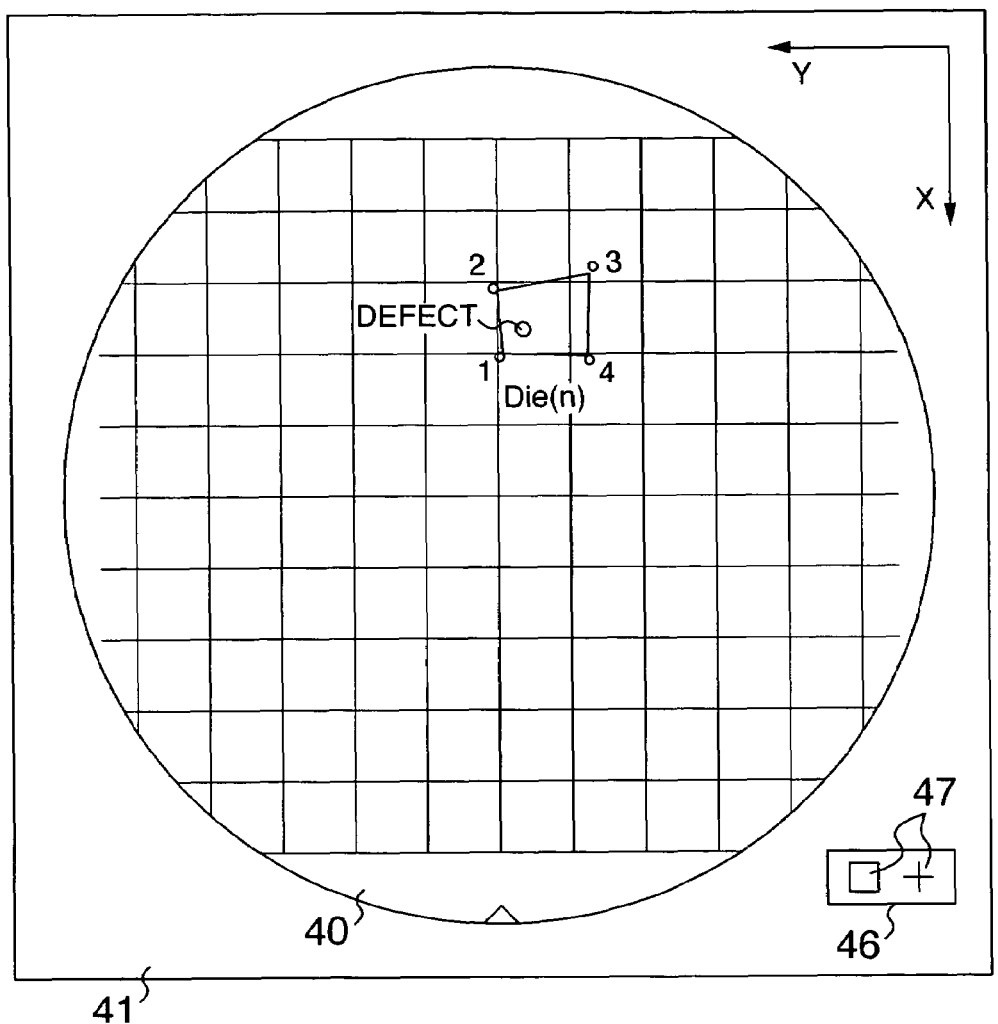
FIGS. 5A and 5B are schematic views of a wafer holder that holds a wafer.
Figure 5B:
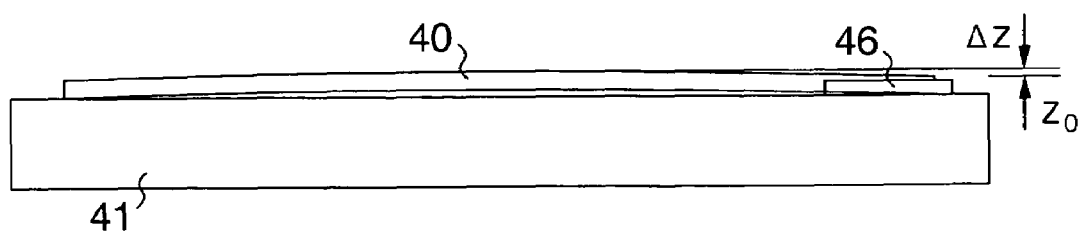

FIG. 5 is a schematic view of the wafer holder holding the wafer. FIG. 5A is a plan view and FIG. 5B is a side view. A portion 46 having the visual field adjustment mark 47 is provided to the wafer holder 41 at a portion other than its wafer placement surface. The height of the portion 46 having the visual field adjustment mark is preferably and substantially equal to the height of the wafer 40. A 90° rotation object figure such as ○□X+◇ etc is provided as the visual field adjustment mark 47 as shown in FIG. 6A. When the 90° rotation object figure is used as the visual field adjustment mark 47, such a figure can be advantageously recognized as the figure having the same shape in the gradient columns different in the 90° direction, that is, in the SEM column and the FIB column. FIGS. 6B, 6C and 6D show a diamond shape as an example and respectively illustrate the figure when viewed from above, the figure when viewed from the oblique 45° direction and the figure when viewed from the oblique 45° direction after 90° rotation.

Figure 7:
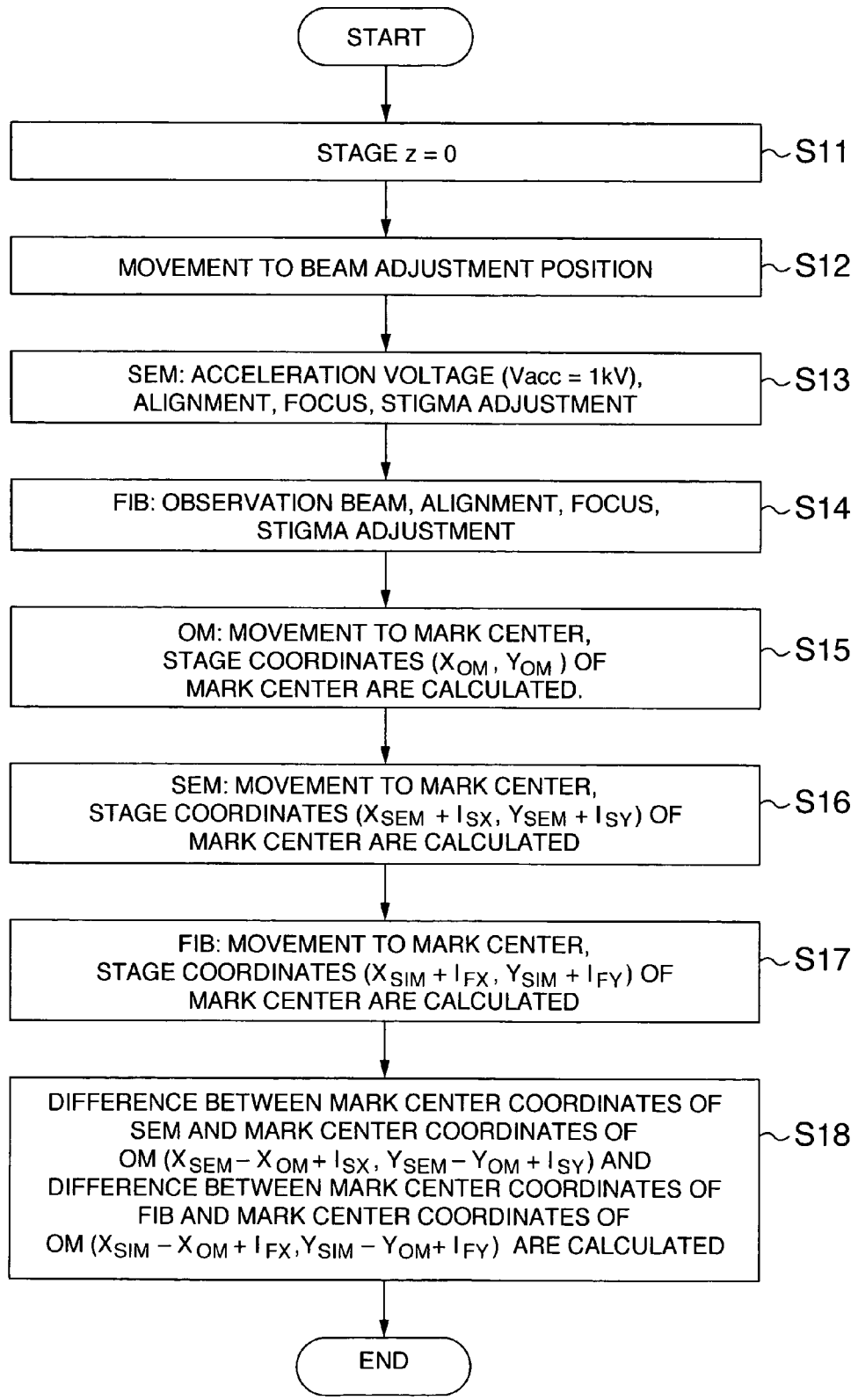
FIG. 7 is a flowchart showing a procedure of an alignment method according to the invention.

Next, the procedure of the alignment method according to the invention will be explained with reference to the flowcharts shown in FIGS. 7 and 8. This alignment can be made automatically, too.

In Step 11 in FIG. 11, the position of the stage in the Z (driving axis in perpendicular direction) direction position is set to the reference position such as Z=0. At this time, the height of the visual field adjustment mark 47 is the reference height. In Step 12, movement is made to the portion 46 to which the visual field adjustment mark 47 is provided. In Step 13, beam alignment, focus and stigma of SEM are adjusted on the portion 46 provided with the visual field adjustment mark 47. In Step 14, beam alignment, focus and stigma of FIB are likewise adjusted.

After this adjustment, the flow proceeds to Step 15 where the image visual field of the optical microscope (OM) is moved to the visual field adjustment mark (for example, □) 47 on the portion 46 and focus is established. The stage coordinates (Xom, Yom) of the center of the mark are calculated. Next, the flow proceeds to Step 16 where the same mark is observed by SEM and the stage coordinates (XSEM+Isx, YSEM+ISY) of the mark center are calculated. Here, the capital I represents an image shift. Next, the flow proceeds to Step 17 where the same mark is observed by FIB and the stage coordinates (XSIM+IFx, YSIM+IFY) of the mark center are determined. The difference (XSEM−XOM+ ISX, YSEM−YOM+ISY) between the mark center coordinates of SEM and the mark center coordinates of OM with OM being the reference and the difference (XSIM−XOM+ IFX, YSIM−YOM+IFY) between the mark center coordinates of FIB and the mark center coordinates of OM are determined. The differences so determined are stored as the offset of the visual field between OM and SEM and the offset of the visual field between OM and FIB in the storage portion of the apparatus. The procedure described so far is the initial adjustment.

Figure 8:
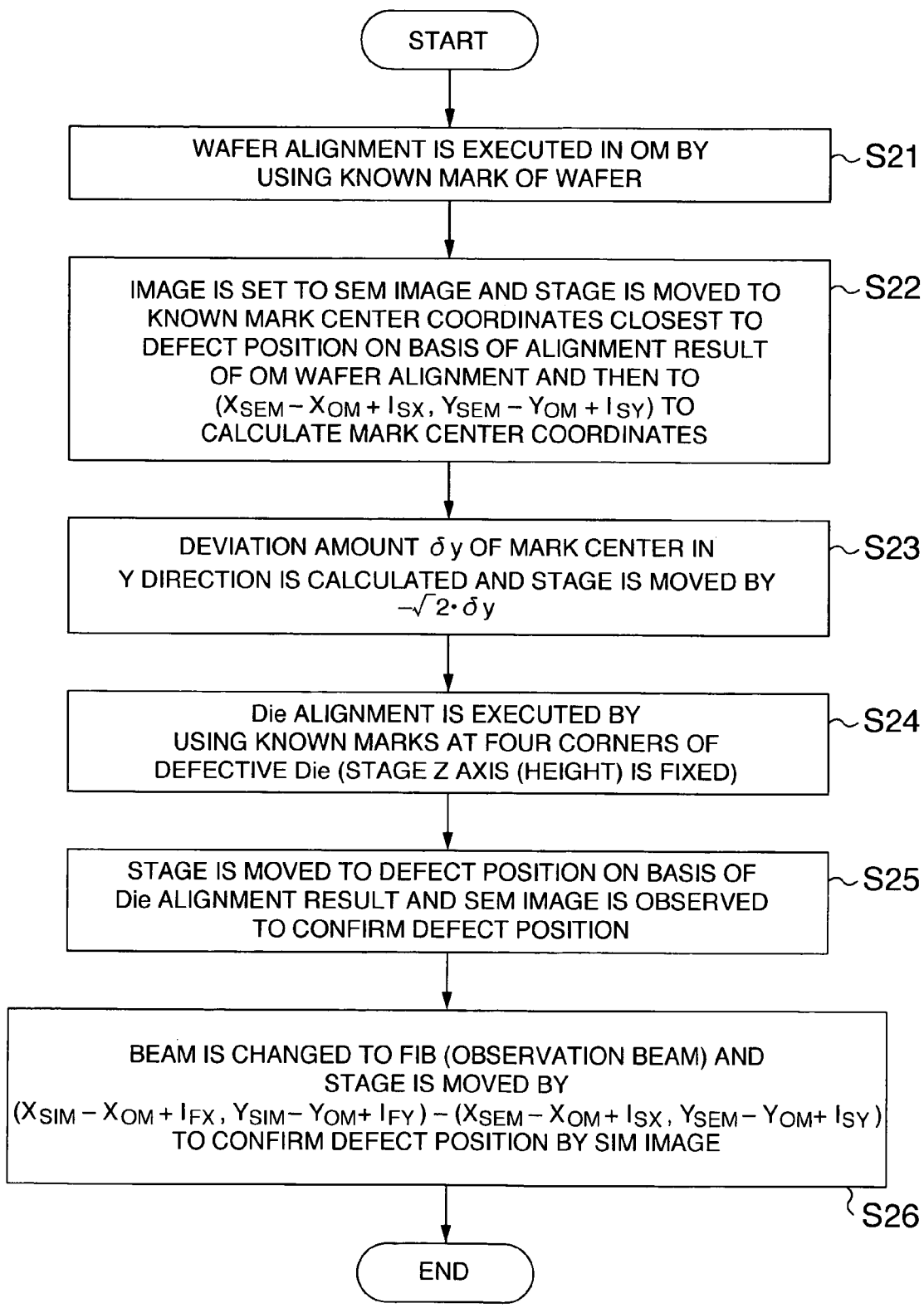
FIG. 8 is a flowchart showing a procedure of the alignment method according to the invention.

Next, movement is made to the defect positive inside the wafer surface detected by the inspection apparatus and observation by SEM or processing by FIB is made in accordance with the flowchart shown in FIG. 8.

In the initial Step 21, wafer alignment is made through OM by using a known mark of the wafer. Next, the flow proceeds to Step 22 where the image is set to the SEM image and movement is made to the center coordinates of the known mark closest to the defect position on the basis of the OM wafer alignment result. Movement is then made by the offset (XSEM−XOM+Isx, YSEM−YOM+ISY) and the coordinates of the mark center are determined. In Step 23, a deviation amount δy of the mark center in the Y direction is determined. This deviation amount δy is the difference from the reference height. Therefore, when the stage Z axis is moved by −√2·δy, the mark center becomes the image center. Consequently, the position close to the mark center can be set to the reference height. In the next Step 24, later-appearing Die alignment is made by using known marks at four corners of a defect Die (or Shot) without changing the height of the stage. Next, in Step 25, the stage is moved to the defect position on the basis of the result of Die alignment and observation is made in the SEM image to confirm the defect position. At this time, the defect can be displayed at the exact center of the visual field.

Next, the flow proceeds to Step 26 where the stage is moved by the offset {(XSIM−XOM+IFY, YSIM−YOM+ IFY)−(XSEM−XOM+Isx, YSEM−YOM+ISY) and observation is made in the SIM image by changing the beam to FIB (observation beam). In this way, the defect can be displayed inside the visual field. When the FIB beam is changed to the processing beam and section processing or sampling processing of the defect position is made by FIB, section processing of the defect portion, etc can be made smoothly. Next, the visual field is moved by the offset of the visual fields between SEM and FIB, the processed portion can be observed through SEM.

Figure 4:
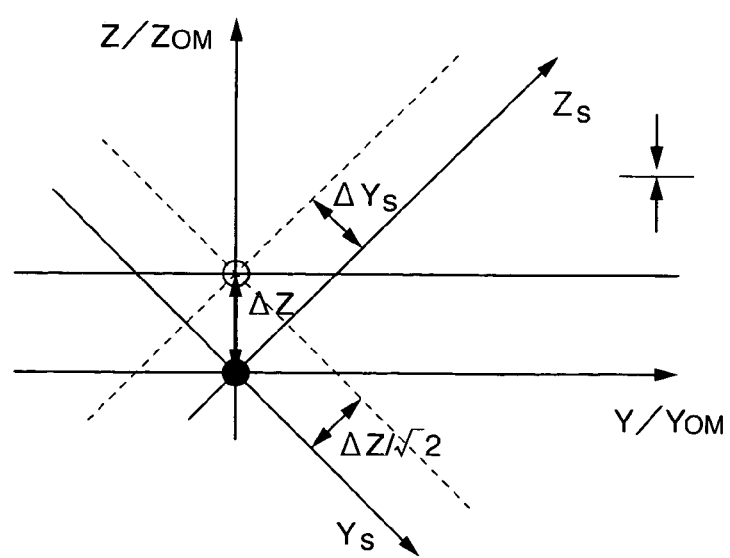
FIG. 4 is an explanatory view of a coordinates system of a vertical column and a coordinates system of the gradient column.

The explanation will be further made quantitatively with reference to FIG. 4. Because the magnification is about 100 times, OM alignment accuracy is low but about ±3 μm can be obtained. Therefore, when the mark position (X, Y) after OM alignment is observed through SEM, an error range of about 3 μm exists in the X direction. Assuming that the ΔZ mark exists at a high position from the reference height (for example Zs=0) owing to the influences of the warp of the wafer, deviation occurs from the screen center (ΔYs). Since ΔYs=−ΔZ/√2 in the case of the 45° gradient, the Ys coordinates change to ΔYs−ΔZ'/√2 when Z of the stage is changed by ΔZ'=√2·ΔYs and the mark can thus be set to the screen center.

When the known mark (device exposure positioning mark) inside the wafer is used, wafer alignment and Die alignment can be carried out automatically. When the mark of the 90° rotation object figure is used for aligning the visual field, the figure can be recognized as the figure having the same shape in the gradient column different in the 90° direction and automatic alignment becomes easier.

Next, Die alignment will be explained. Die alignment (Die(n) shown in FIG. 5A) detects the mark center by serially moving to the predetermined mark positions at the four corners (that are formed at correct positions for positioning of a device fabrication device in accordance with the design of the semiconductor device) for each Die, calculates distortions from the four corners and a transform formula for correctly converting the distortions to the four corners, on the contrary. In consequence, it becomes possible to move the stage to the correct defect position on the basis of the defect data determined by the inspection apparatus in the gradient column apparatus.

The measurement data of the inspection apparatus determines the defect position with respect to the Die origin for each die. Therefore, the coordinates system of the Die and the transform formula of the coordinates system of the observation apparatus can be obtained from the mark positions at the four corners of the Die so decided.

$$\begin{pmatrix} X0 \\ X1 \\ X2 \\ X3 \end{pmatrix} = \begin{pmatrix} 1 & Xw0 & Yw0 & Xw0 \cdot Yw0 \\ 1 & Xw1 & Yw1 & Xw1 \cdot Yw1 \\ 1 & Xw2 & Yw2 & Xw2 \cdot Yw2 \\ 1 & Xw3 & Yw3 & Xw3 \cdot Yw3 \end{pmatrix} \begin{pmatrix} a0 \\ a1 \\ a2 \\ a3 \end{pmatrix} \quad \text{[Expression 3]}$$

$$\begin{pmatrix} Y0 \\ Y1 \\ Y2 \\ Y3 \end{pmatrix} = \begin{pmatrix} 1 & Xw0 & Yw0 & Xw0 \cdot Yw0 \\ 1 & Xw1 & Yw1 & Xw1 \cdot Yw1 \\ 1 & Xw2 & Yw2 & Xw2 \cdot Yw2 \\ 1 & Xw3 & Yw3 & Xw3 \cdot Yw3 \end{pmatrix} \begin{pmatrix} b0 \\ b1 \\ b2 \\ b3 \end{pmatrix}$$

Here, (Xi, Yi) (i=0 to 3) is the coordinates obtained by mark detection and (Xwi, Ywi) (i=0 to 3) is the mark position (mark design coordinates) of the Die.

When the inverse matrix of the matrix described above is calculated, the transform coefficient (ai, bi) (i=0 to 3) of the formula described above can be easily calculated. The defect position (Xwj, Ywj) from the inspection apparatus can be converted to (uj, vj) by the following formula.

$$\begin{pmatrix} uj \\ vj \end{pmatrix} = \begin{pmatrix} a0 & a1 & a2 & a3 \\ b0 & b1 & b2 & b3 \end{pmatrix} \begin{pmatrix} 1 \\ Xwj \\ Ywj \\ Xwj \cdot Ywj \end{pmatrix}$$ [Expression 4]

When the stage is moved in accordance with this formula, the defect position can be easily moved to a position immediately below the beam. However, Z and R of the stage do not move at this time. The transform formula so obtained can be used substantially in the same way even when the Die is somewhat different as long as the Die exists inside the same wafer. Therefore, it will be sufficient to once determine (ai, bi) (i=0 to 3) by calculation.

The explanation given above has been made on the assumption that SEM alignment is made. However, alignment using FIB (SIM alignment) can be made in the same way as the SEM alignment by replacing X and Y in the explanation.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A charged particle beam apparatus comprising:
   a stage capable of moving inside an XY plane and in a Z axis direction perpendicular to said XY plane while holding a sample;
   a first column having an optical axis parallel to said Z axis;
   a second column having an optical axis inclined to said Z axis; and
   a control portion for processing a visual field image by said first column and a visual field image by said second column and controlling the movement of said stage;
   wherein a mark for aligning visual fields between said first column and said second column is formed on said stage.

2. A charged particle beam apparatus as defined in claim 1, wherein said mark for aligning the visual fields is figures having symmetry of rotation of 90°.

3. A charged particle beam apparatus as defined in claim 1, wherein a portion on which said mark for aligning the visual fields is disposed on a wafer holder for holding a wafer.

4. A charged particle beam apparatus as defined in claim 1, wherein a difference between stage coordinates of said mark observed by said first column and stage coordinates of said mark observed by said second column under the condition where a height of said mark for aligning the visual fields is set to a reference height in said Z direction is stored as an offset of the visual field of said first column and the visual field of said second column.

5. A charged particle beam apparatus as defined in claim 1, wherein said second column is a focused ion beam and/or a scanning electron microscope.

6. A charged particle beam apparatus as defined in claim 5, wherein an optical axis of said focused ion beam and an optical axis of said scanning electron microscope are inclined at 45° with respect to said Z axis and an intersecting angle of said optical axes is 90°.

7. A charged particle beam apparatus as defined in claim 1, wherein said first column is an optical microscope.

8. An alignment method in a charged particle beam apparatus including a stage capable of moving inside an XY plane and in a Z axis direction perpendicular to said XY plane while holding a sample, a first column having an optical axis parallel to said Z axis and a second column having an optical axis inclined to said Z axis, said method comprising the steps of:
   positioning a mark at a reference height to a visual field center of said first column and calculating stage coordinates of said mark;
   positioning said mark to a visual field center of said second column and calculating the stage coordinates of said mark; and
   determining a difference between the stage coordinates of said mark by said first column and the stage coordinates of said mark by said second column as an offset between the visual field of said first column and the visual field of said second column.

9. An alignment method as defined in claim 8, further comprising the steps of:
   moving said stage inside the XY plane and positioning a known mark on a sample to the visual field center of said first column;
   moving said stage by said offset;
   observing said known mark by said second column and determining a deviation amount from the visual field center;
   determining a height deviation of the sample from said reference height on the basis of said deviation amount; and
   moving said stage by the height deviation in the Z axis direction and adjusting a sample surface provided with said known mark to said reference height.

10. An alignment method in a charged particle beam apparatus including a stage capable of moving inside an XY plane and in a Z axis direction perpendicular to said XY plane while holding a sample, an optical microscope having an optical axis parallel to said Z axis, a first column having an optical axis inclined at 45° with respect to said Z axis inside a YZ plane and a second column having an optical axis inclined at 45° with respect to said Z axis inside an XZ plane, said method comprising the steps of:
   positioning a mark existing at a reference height to a visual field center of said optical microscope and calculating stage coordinates of said mark;
   positioning said mark to a visual field center of said first column and calculating the stage coordinates of said mark;
   positioning said mark to a visual field center of said second column and calculating the stage coordinates of said mark; and
   determining a difference between the stage coordinates of said mark by said optical microscope and the stage coordinates of said mark by said first column as a first offset and determining a difference between the stage coordinates of said mark by said optical microscope and the stage coordinates of said mark by said second column as a second offset.

11. An alignment method as defined in claim 10, further comprising the steps of:
   moving said stage inside the XY plane and positioning a known mark on a sample to the visual field center of said optical microscope;
   moving said stage by said first offset;

observing said known mark by said first column and calculating a deviation amount ΔY from the visual field center in the Y direction; and moving said stage by $-\sqrt{2}\cdot\Delta Y$ in the Z axis direction and adjusting the sample surface on which said known mark is disposed to said reference height.

12. An alignment method as defined in claim 11, further comprising the steps of:

moving said stage by said second offset after observation by said first column; and observing said sample by said second column.

13. An alignment method as defined in claim 10, wherein said first column is a scanning electron microscope and said second column is a focused ion beam apparatus.

* * * * *